United States Patent [19] [11] 4,239,702
deWitt et al. [45] Dec. 16, 1980

[54] PROCESS FOR PREPARING AROMATIC ALDEHYDES AND ALCOHOLS

[75] Inventors: Paolo deWitt; Maria O. Tinti, both of Rome, Italy

[73] Assignee: Sigma-Tau Industrie Farmaceutiche Riunite S.p.A., Italy

[21] Appl. No.: 4,447

[22] Filed: Jan. 18, 1979

[30] Foreign Application Priority Data

Jan. 27, 1978 [IT] Italy .............................. 47811 A/78
Jan. 4, 1979 [IT] Italy .............................. 47537 A/79

[51] Int. Cl.$^3$ ..................... C07C 45/29; C07C 29/136
[52] U.S. Cl. .................................. 568/435; 260/363; 568/814; 568/648
[58] Field of Search ................... 250/600, 599, 363; 568/814, 648

[56] References Cited

U.S. PATENT DOCUMENTS

| 2,883,426 | 4/1959 | Brackman | 260/599 X |
| 3,322,833 | 5/1967 | McNelis | 260/599 |
| 3,855,306 | 12/1974 | Wehrli | 260/600 |
| 3,978,140 | 8/1976 | Lane et al. | 568/814 X |

FOREIGN PATENT DOCUMENTS 1123664 6/1956 France ..................................... 568/814

OTHER PUBLICATIONS

Tarbell et al., Jour. Org. Chem., vol. 23 (1958) 1149–1152.
Tarbell, Accounts of Chemical Research 2(10) 1969 290, 297–300.
Tarbell et al., Chemical Abstracts, vol. 50 (1956) 14727f.

Primary Examiner—Bernard Helfin
Attorney, Agent, or Firm—McGlew and Tuttle

[57] ABSTRACT

Process for the production of aromatic alcohol and aldehydes comprising three steps, the first one consisting of reacting an aromatic acid with ethyl or isobutyl chloroformiate to obtain the corresponding mixed anhydride, the second one consisting of the hydrogenation of the mixed anhydride to obtain the corresponding benzyl alcohol, and the third one consisting of the oxidation of the alcohol to the corresponding aldehyde.

5 Claims, No Drawings

PROCESS FOR PREPARING AROMATIC ALDEHYDES AND ALCOHOLS

FIELD AND BACKGROUND OF THE INVENTION

The present invention relates to a general process for preparing aromatic aldehydes and alcohols. More particularly, it relates to the preparation of benzaldehyde and benzilic alcohol, and of derivatives thereof, like for instance 3,4,5-trimethoxybenzaldehyde and 3,4,5-trimethoxy benzyl alcohol.

The industrial utility of benzaldehyde in the manufacture of colouring and aromatizing substances as intermediate in the production of cinnamic and mandelic acid and as solvent is well-known, while benzyl alcohol is used, for instance, as bacteriostatic and solvent for gelatine, casein and cellulose acetate. In particular, 3,4,5-trimethoxybenzaldehyde is a valuable intermediate in the synthesis of many pharmaceutical products, especially in the production of 2,4-diammino-5-(3,4,5-trimethoxy)benzyl-pyrimidine (trimethoprim).

In view of the importance, for the pharmaceutical industry, of the synthesis of 3,4,5-trimethoxybenzaldehyde and of the well-known difficulties and disadvantages (which will be illustrated in detail hereinafter) carried by the traditional processes of synthesis of this intermediate, the process for the production of aromatic alcohols and aldehydes of the present invention will be particularly described with reference to the synthesis of the benzaldehyde derivative. It is to be understood, as it is illustrated in the examples and evident for anyone skilled in organic synthesis, that the present process has a general character and can be used, choosing the suitable raw material, for the preparation of other aromatic aldehydes and alcohols.

The two industrial processes that are more widely used for producing 3,4,5-trimethoxybenzaldehyde are both unsatisfactory, both because of the very high cost of the desired product and of the poor yields of the reactions involved in these processes.

The first process is based on the Rosemund reduction of 3,4,5-trimethoxy benzoic acid chloride and the second one consists in the bromuration of vanilline, followed by methylation of the hydroxyl group in position 4 in respect to the carbonyl and in the simultaneous substitution of the bromine atom with a methoxyl group.

This second process is described by patent U.S. Pat. No. 3,855,306. The process based on the catalytic hydrogenation of 3,4,5-trimethoxybenzoic acid chloride, following the method of Rosemund, in aromatic solvents containing a poison of the catalyst, was studied by several authors. But no one of them overcame the very heavy inconveniences (from the industrial point of view) connected with the yields, which are neither very high nor constant (50–80% of the theory).

Other processes which have been described are transformations of 3,4,5-trimethoxybenzoic acid chloride in 3,4,5-trimethoxybenzaldehyde with yields of 64–83% of distilled product by means of a variation of the Rosemund process, that is in presence of sodium acetate as a hydrogen ion acceptor. In this process the reduction of 3,4,5-trimethoxybenzoic acid chloride must be carried out in the presence of a disactivant (solvent toluene) like sulphur-quinoline and sodium acetate on palladiate charcoal (5%) during many hours at room temperature and 2 hours at 50° C. and 50 psi of hydrogen. In several experiments carried out in the above described conditions, a product of 84% purity with a yield of 72–74% has been obtained.

Moreover, it is pointed out that, whereas 3,4,5-methoxybenzoic acid, which is the raw material for the preparation of the chloride, is easily found on the market at a reasonable cost, the chloride, obtained from the acid by treatment with thionyl chloride is not easily prepared on an industrial scale, especially because the subsequent Rosemund hydrogenation requires a product of high grade of purity. In fact, on the market the chloride of 3,4,5-trimethoxybenzoic acid has a price which is two times higher than the one for the starting acid.

In conclusion, the 3,4,5-trimethoxy-benzaldehyde prepared by the Rosemund more or less modified method has by far, too high a price for a starting material for the production of drugs, which are indispensable for large widespread consumption.

The process described in the patent U.S. Pat. No. 3,855,306 comprehend the prepartion of 5-bromovanillin starting from vanillin. The cost of vanillin is already higher than that for 3,4,5-trimethoxybenzoic acid; however the reaction proceeds easily and with high yields (about 98% of theoretical).

From the 5-bromo derivative, by treating it with KOH and methanol, the 3,4,5-trimethoxybenzaldehyde is obtained. The yields however, of that step are not economically acceptable. There are no better results where the methylation of 5-bromo vanillin and substituting afterwards the bromine atom with the methoxy group are carried out separately.

Using the method which utilize vanillin as a starting material, we are unable to obtain 3,4,5-trimethoxy benzaldehyde at an acceptable cost.

The reduction operations which leads from the 3,4,5-trimethoxy benzoic acid to the corresponding aldehyde directly by means of metallic hydrides give an even more costly product. Experiments carried out with the aim to directly introduce the carbonyl group in the pyrogallol or in the trimethoxybenzene failed, since the carbonyl group does not enter in the requested position.

It is well known in organic chemistry how possible it is, also on an industrial scale, to produce aldehydes from alcohols by means of oxidations with suitable oxidative agents. If this method is applied to the 3,4,5-trimethoxybenzaldehyde for big productions, the chief problem is obtaining 3,4,5-trimethoxybenzyl alcohol at low cost.

SUMMARY OF THE INVENTION

The applicants have solved the foregoing problem by preparing the wanted alcohol by catalitic reduction of 3,4,5-trimethoxy-benzoyl-ethyl carbonate which was directly prepared from 3,4,5-trimethoxy benzoic acid and ethyl chloroformate. The raw materials for the preparation of the mixed anhydride (that is the 3,4,5-trimethoxybenzoyl-ethyl carbonate) are easily found at low cost on the market, since they are industrial products.

The reaction proceeds in very mild conditions (atmospheric pressure and 5°–10° C. temperature) with a very high yield (90–95% of theoretical. Just for this reason this reaction is largely used in synthetical chemistry. The fact that, was not known up to now, is that 3,4,5-trimethoxy-benzoyl-ethyl carbonate can be directly catalytically hydrogenated giving the corresponding benzyl alcohol. Operating in well determined conditions of pressure and temperature, high yields have been obtained and the cost of the alcohol is much lower than that of the same alcohol prepared by known methods.

From this discovery, the 3,4,5-trimethoxy benzyl alcohol is not to be considered any longer as a valuable reagent, but it becomes now an industrial product. Moreover, since by using very simple oxidation methods, the applicants obtained the corresponding aldehyde from the alcohol, it is possible now to offer 3,4,5-trimethoxy benzaldehyde at a cost which is remarkably lower than the prices charged today. The preparation of the mixed anhydride is carried out in tetra hydrofuran or in benzene or in any other anhydrous inert solvent.

If we operate in solvents which are inert against catalytic hydrogenation, as tetrahydrofuran is, we can avoid the isolation of the mixed anhydride and can directly proceed to the hydrogenation.

3,4,5-trimethoxy benzoic acid and ethylchloroformate are mixed in the presence of trimethylamine (or of any other anhydrous organic base) at a temperature between $+5°$ and $+10°$ C. Outside this temperature limits, a decrease of the yields are observed. The mixture is kept under stirring during some hours, the triethylamine hydrochloride (or the hydrochloride of any other base employed) is filtered off and, if the operation was carried out in a solvent which is proof against catalytic hydrogenation, we can directly proceed to this last mentioned operation.

As catalyst, a 5% palladium charcoal in amounts of 1–5 g/0.10 moles of 3,4,5-trimethoxy benzoic acid is preferred. The most favourable temperature range is 55°–65° C. The most favourable pressure range is 150–250 psi. The most favourable reaction time is 8–12 hours, and preferably a 10 hour period. The reaction time is very important, because this has an influence on the formation of secondary products.

Operating by the described conditions, we obtain yields, in respect to the starting acid, of 85–90% of the theoretical, of pure product. The identity, the purity degree, the nature of the secondary components of the hydrogenation product are identified by TLC, gas chromatography, NMR and HPLC.

More generally, according to the present invention, the process for producing aromatic alcohols and aldehydes, in particular benzyl alcohol, benzaldehyde and derivatives thereof, comprises the following steps:

(1) to react at 5°–10° C., at atmospheric pressure, an aromatic acid choosen in the class formed by benzoic acid and derivatives thereof, such as benzoic acid substituted with, lower alkyl- and lower alkoxy-groups, chlorine and bromine according to the method of mixed anhydrides, with ethyl or isobutyl chloroformate, in the presence of an anhydrous base and an anhydrous solvent, inert with respect to the reagents, obtaining the corresponding mixed anhydride;

(2) To hydrogenate directly the mixed anhydride of step (1) at 55°–65° C., at 150–250 pound/inch (10.5–17.5 Kg/cm$^2$), for 8–12 hours in the presence of a hydrogenation catalyst, preferably 5% palladium on charcoal, obtaining the corresponding benzyl alcohol; and (3) to oxidize the benzyl alcohol of step (2) to the corresponding aldehyde.

The following, non-limitative example are a further elucidation of the invention.

EXAMPLE I 3,4,5-trimethoxybenzoyl-ethyl-carbonate.

g 10.8 (0.10 moles) of ethylchloroformate in 100 ml tetrahydrofuran are added, under stirring and by cooling at 5°–10° C. and during 10–30 minutes to a solution of 21.2 g (0.10 moles) of 3,4,5-trimethoxy benzoic acid and 12.12 (0.12 moles) of triethylamine in 200 ml tetrahydrofuran. At the end of the addition the mixture is kept at room temperature for 2 hours under stirring.

The formed precipitate is filtered, throughtly washed with tetrahydrofuran and discarded.

On the joined reaction solution and washing liquids we can directly proceed to the catalytic reduction for the preparation of 3,4,5-trimethoxy benzyl alcohol (Example II). The 3,4,5-trimethoxybenzoyl-ethyl-carbonate may also be isolated evaporating under a vacuum at a temperature between 50° and 70° C. The residual is a white microcrystalline solid; g 26.7, yield 94% with following characteristics: m.p. 92°–94° C.

IR spectrum = 1810 and 1710 cm$^{-1}$

NMR spectrum (CD$_3$)$_2$SO $\delta$ 7.4 (s, 2H, aromatics); 4.4 (q, 2H, $\underline{CH_2}$—CH$_3$); 3.9 (s, 6H, 3.5—OCH$_3$); 3,8 (s,3H, 4—$\overline{OCH_3}$); 1.35 (t, 3H, CH$_2$—$\underline{CH_3}$)

Anal. C = 54.85%, H = 5.34%.

The product is remarcably stable and keeps well also at room temperature. It is not affected by moisture.

EXAMPLE II 3,4,5 trimethoxybenzyl alcohol.

To a solution of 3,4,5-trimethoxybenzoyl-ethyl-carbonate (0.1 moles), prepared as described in example I, 100 ml of glacial acetic acid and 5 g of 5% palladium on C (5% Pd/C ENGELHARD) are added.

The mixture is reduced in a PARR type apparatus during 10 hours at 60° C. under a pressure of (200 psi 14 tm) hydrogen. The catalyst is filtered off and washed with 100 ml of tetrahydrofuran. The joined filtrates are treated with 500 ml cold water, adjusted at pH 5 and saturated with NaCl. The organic solution of tetrahydrofuran which is separated, is concentrated in a vacuum. A yellow, semisolid product of 30.46 g is obtained. The TLC chromatography show the presence, in this mixture, of 3,4,5-trimethoxy benzyl alcohol and of 3,4,5-trimethoxy benzoic acid plus traces of 3,4,5-trimethoxy benzaldehyde.

The crude product is treated with 200 ml of CHCl$_3$ and 200 ml of 5% NaOH solution.

The isolated acid fraction contains g 2.58 (12%) of 3,4,5-trimethoxy benzoic acid, whereas the organic phase of chloroform contains a non acid fraction consisting chiefly of 3,4,5-trimethoxy benzyl alcohol. After evaporation of the solvent, g 16.30 (83%) of a dense, slightly yellow liquid are obtained. B.P. 225° C./25 mm Hg, d = 1.23.

The substance has following NMR characteristics (CDCl$_3$):

$\delta$ 6.59 (s, 2H, aromatics); 4.2 (d, 2H, $\underline{CH_2}$—OH); 3.90 (s, 9H, 3 OCH$_3$); and 2.1 (t, iH,—$\underline{OH}$)

EXAMPLE III 3,4,5-trimethoxybenzaldehyde (from 3,4,5-trimethoxybenzyl alcohol)

33.9 g (0.34 moles) of chromic anhydride are slowly dissolved under efficient stirring in 500 ml of glacial acetic acid and heating at 90°–100° C.

To this oxydation mixture, g 19.8 of 3,4,5-trimethoxy benzyl alcohol dissolved in 160 ml of glacial acetic acid are very slowly added under continuous stirring. The mixture is kept reacting during 30' after the end of the addition and is then cooled, diluted with water and extracted with CHCl₃ (3 fractions of 200 ml each).

The organic fractions are then joined and concentrated under a vacuum. Obtained are g 17.60 (90%).

M.P. 38°–40° C.; B.P., 168°–170° C./12 mm.

NMR spectrum: (CDCl₃) δ 9.82 (s, 1H, —CHO); 7.1 (s, 2H, aromatics) and 3.95 (s, 9H, 3 OCH₃).

EXAMPLE IV 3,4,5-trimethoxybenzaldehyde (from 3,4,5-trimethoxybenzyl alcohol)

g 63.2 of KMnO₄ are dissolved at room temperature and under stirring in 1500 ml H₂O. A solution containing 150 g of Na₂SO₃.7H₂O in 400 ml water is slowly added. The mixture is stirred at room temperature during 2 hours and the MnO₂ formed is filtered in order to obtain a nearly dry product. The MnO₂ is suspended in ml 450 of CHCl₃.

To this suspension 39.6 g (0.2 moles) of 3,4,5-trimethoxy benzyl alcohol are directly added and the mixture is stirred during 8 hours at 25° C.

The solid is filtered and discarded whereas the organic solution is concentrated in a vacuum to dryness. 37.7 g of a semi solid product having the same characteristics of the one described in example III are obtained.

EXAMPLE V

Benzoyl-ethyl-carbonate 10.8 g (0.10 moles) of ethylchloroformiate dissolved in 100 ml of tetrahydrofuran are added to a solution of tetrahydrofuran (200 ml) containing 12.2 g (0.10 moles) of benzoic acid and 12.12 g (0.12 moles) of triethylamine.

We proceed as in Example I.

We obtain 17.8 g (yield 92%) of a product having the following characteristics:

Elementary analysis C=61.85% H=5.19%

Spectrum NMR: (CD₃)₂SO δ 8.2–7.4 (m, 5H, aromatics); 4.4 (q, 2H, —CH₂—CH₃) 1.3 (t, 3H, —CH₂—CH₃)

EXAMPLE VI

Benzyl alcohol 100 ml of glacial acetic acid and 5 g of 5% palladium on charcoal are added to a solution of benzoyl-ethyl carbonate (20.8 g=0.1 moles) in 300 ml of tetrahydrofuran.

The mixture is reduced in a PARR type device for 10 hours at 60° C. and under a pressure of 200 psi (14 atm.) of H₂. We proceed as in Example II. We obtain 8.6 g (yield 80%) of a liquid, having the following characteristics:

B.P.=205° C.
d=1,045
n_D=1.5403

Spectrum NMR: δ 7.3 (s, 5H aromatics); 4.7 (s, 2H, —CH₂—OH); 1.8 (s, 1H, —CH₂—OH).

EXAMPLE VII

Toluyl-ethyl carbonate 10.8 g (0.10 moles) of ethychloroformiate dissolved in 100 ml of tetrahydrofuran are added to a solution of tetrahydrofuran (100 ml) containing 13.6 g (0.10 moles) of toluic acid and 12.12 g (0.12 moles) of triethylamine. We proceed as in Example I.

We obtain g 18.7 (yield 90%) of a product having the following characteristics:

Elementary analysis C=63.45%, H=5.80%.

Spectrum NMR: (CD₃)₂SO δ=8.0 (d, 2H, aromatics); 7.2 (d, 2H, aromatics); 2.4 (s, 1H, CH₃—); 4.4 (q, 2H, —CH₂—CH₃); 1.3 (t, 3H, —CH₂—CH₃).

EXAMPLE VIII

Methyl-benzyl alcohol 100 ml of glacial acetic acid and 5 g of 5% Pd on C are added to a solution of toluyl-ethyl-carbonate (20.8 g=0.10 moles) in 300 ml of tetrahydrofuran. The mixture is reduced in a PARR apparatus for 10 hours at 60° C. and under a pressure of 200 psi (14 atm) of H₂.

We proceed as in Example II.

We obtain 9.7 g (yield 80%) of a product having the following characteristics:

M.P. 59°–61° C.

Spectrum NMR: (DMSO) δ 7.2 (s, 4H, aromatics); 4.6 (s, 2H, —CH₂—OH); 2.3 (s, 3H, —CH₃); 1.9 (s, 1H, —CH₂—OH).

EXAMPLE IX p-chlorobenzoyl-ethyl carbonate 10.8 g (0.10 moles) of ethylchloroformiate dissolved in 100 ml of tetrahydrofuran are added to a solution of tetrahydrofuran (200 ml) containing 15.6 g (0.10 moles) of p-chloro-benzoic acid and g 12.12 (0.12 moles) of triethylamine. We proceed as in Example I.

We obtain g 21 (yield 92%) of a product having the following characteristics:

Elementary analysis C=52.53%, H=3.96%.

Spectrum NMR: (CD₃)₂SO δ=7.9 (d, 2H, aromatics); 7.4 (d, 2H, aromatics); 4.4 (q, 2H, —CH₂—CH₃); 1.3 (t, 3H, —CH₂—CH₃).

EXAMPLE X p-chlorobenzyl-alcohol 100 ml of glacial acetic acid and 5 g of 5% Pd on C are added to a solution of p-chlorobenzoyl-ethyl carbonate (22.8 g=0.1 moles). The mixture is reduced in a PARR apparatus for 10 hours at 60° and under a pressure of 200 psi (14 atm) of H₂. We proceed as in Example II. We obtain 11.7 g (82%) of a product having the following characteristics:

M.P. 70°–72° C.

Spectrum NMR: (DMSO) δ=7.2 (s, 4H aromatics) 4.6 (s, 2H, CH₂—OH) 2.1 (s, 1H, CH₂—OH)

It was found, moreover, that it was advantageous, both because of the lower cost of the oxidizer and of the substantial absence of problems of pollution, to carry out the oxidation of step (3) from alcohol to aldehyde using as oxidizing agent an aqueous solution of a compound which liberates, in solution, hypochlorite (ClO⁻) in the presence of a phase transfer catalyst.

This catalyst is preferably choosen among the quaternary ammonic salts formed by three hydrocarbonyl C₈–C₁₀ and by a methylic group.

Catalysts of this kind are, for instance, the ones put onto the market by Fluka with the trademark ALIQUAT-336 and by Aldrich with the trademark ADOGEN-464. One skilled in the art will be able to find, on the basis of what is above taught, other phase transfer catalysts suitable for use in the present process among the ones available on the market at present. In these recent years the phase transfer catalysis has been the object of a remarkable interest, above all with reference to the fact that, utilizing the above methods, reactions that otherwise would require the use of costly anhydrous solvents are made economically convenient. The conditions of the phase transfer, instead, require that the reactions are carried out, generally in mild conditions, in a diphasic ambient water/organic solvent. In practice, in most of its appliances, a cation having sufficiently lipophilic characteristics (generally ammonium-ion, but also phosphonium, solphonium ions, etc.) transfers from the aqueous to the organic phase an anion which, reacting, leaves the cation free to carry out its work again.

According to this scheme, numerous reactions were described, among which various oxidation reactions wherein $MnO_4^-$, $HCrO_4^-$ ions were transferred from the aqueous phase to the organic phase, as salts with quaternary ammonium ions. Also the oxidation of alcohols with $ClO^-$ in conditions of phase transfer was described. In this connection see, for instance: "Phase Transfer Catalyzed Oxidations of Alcohols and Amines by Acqueous Hypochlorite", G. A. Lee, H. H. Freedman Tetrahedron Letters, (20) 1641; 1967.

In this article, the teachings of which are incorporated by reference in the present specification, a different transfer catalyst is used, however, as well as different operation conditions with respect to the ones being the object of the present invention.

The following further non-limitative examples are an elucidation of this variant of the process of the present invention.

EXAMPLE XI

Preparation of benzaldehyde.

5 g (46.24 mmoles) of benzyl alcohol dissolved in 100 ml of $CH_2Cl$ (RPE Carlo Erba) were added to 300 ml of a commercial solution (RPE Carlo Erba) of NaOCl (about 462.5 mmloes) containing 2.80 g (about 6.94 mmoles) of Aliquat-336. The mixture was heated to 40° C. under stirring for 2 hours. It was let return to room temperature, was extracted by $Et_2O$ washing with $H_2O$ to neutrality.

It was anhydrized with $Na_2SO_4$ and a solution containing benzaldehyde was obtained with a yield of 85%. The pure benzaldehyde was obtained by fractioned distillation (total yield 75%).

EXAMPLE XII

Preparation of 3,4,5- trimethoxy-benzaldehyde (A) 5 g (25.25 mmoles) of 3,4,5-trimethoxybenzyl alcohol dissolved in 65 ml of $CHCl_3$ (RPE Carlo Erba) were added to 164 ml of a commercial solution (RPE Carlo Erba) of NaOCl (about 252.5 mmoles) containing 1.52 g (3.79 mmoles) of Aliquat-336. The reaction mixture was kept at 60° C. under stirring for 1 hour. It was let to get back to room temperature, extracted with $Et_2O$ washing with $H_2O$ to neutrality.

It was anhydrized on $Na_2SO_4$ and led to dryness by Rotavapor. 4.630 g of a white raw substance with M.P. 60°-63° C. were obtained.

(B) The reaction was carried out in the conditions mentioned in the previous example, using the same ratios of reagent and solvent but utilizing as phase transfer catalyst Adogen-464. A raw product (about 4.58 g) with M.P. 59°-62° C. was obtained.

EXAMPLE XIII

Preparation of benzophenone.

5 g (27.17 moles) of diphenyl-methanol dissolved in 55 ml of AcOEt (RPE Carlo Erba) were added to 177 ml of a commercial solution (RPE Carlo Erba) of NaOCl (about 271.7 moles) containing 1.65 g (about 4.1 moles) of Aliquat-336.

The reaction mixture was kept at room temperature under stirring for 5 hours. It was extracted with $Et_2C$ washing with $H_2O$ to neutrality, anhydrized with $Na_2SO_4$ and led to dryness by Rotavapor. 4.40 g of a raw solid containing 75% of benzophenone were obtained.

The advantages obtained with respect to the traditional oxidizers, like chromo anhydride and manganese dioxide are immediately evident. These advantages are:
lower cost of the reagent;
less pollution problems;
use of a more manageable solvent; and
higher yields of the desired final products.

What is claimed is:

1. Process for producing a benzyl alcohol comprising the steps of:
   (1) reacting at 5°-10° C., at atmospheric pressure, an aromatic acid chosen in the group formed by benzoic acid or benzoic acid substituted with lower-alkyl radicals, lower alkoxy groups, chlorine and bromine, with ethyl or isobutyl chloroformiate, in the presence of an anhydrous base or an anhydrous solvent, inert in respect to the reagents, obtaining the corresponding mixed anhydride; and
   (2) hydrogenizing by catalysis the mixed anhydride of step (1) at 55°-65° C., at 150-250 pounds/inch$^2$ for 8-12 hours in the presence of a palladium on charcoal hydrogenation catalyst, obtaining the corresponding benzyl alcohol.

2. Process according to claim 1, wherein said hydrogenation catalyst is 5% palladium on charcoal.

3. Process for producing benzaldehyde comprising the steps of:
   (1) reacting at 5°-10° C., at atmospheric pressure, an aromatic acid chosen in the group formed by benzoic acid or benzoic acid substituted with lower alkyl-radicals, lower alkoxy-groups, chlorine and bromine, with ethyl or isobutyl chloroformiate, in the presence of an anhydrous base or an anhydrous solvent, inert in respect to the reagents, obtaining the corresponding mixed anhydride;
   (2) hydrogenizing by catalysis the mixed anhydride of step (1) at 55°-65° C., at 150-250 pounds/inch$^2$ for 8-12 hours in the presence of a palladium on charcoal hydrogenation catalyst, obtaining the corresponding benzyl alcohol; and
   (3) oxidizing the benzyl alcohol of step (2) to the corresponding aldehyde using as oxidizing agent an aqueous solution of a compound which liberates hypochlorite ions in the presence of a phase transfer catalyst, chosen among the quaternary ammonium salts formed by three hydrocarbonic chains $C_8-C_{10}$ and by a methyl group.

4. Process according to claim 3, wherein said hydrogenation catalyst is 5% palladium on charcoal.

5. Process according to claim 3, wherein said catalyst is chosen in the class formed by ALIQUAT-336 and ADOGEN-464.

* * * * *